United States Patent [19]

Miller et al.

[11] 4,320,058

[45] Mar. 16, 1982

[54] 20'-HYDROXYVINBLASTINE AND RELATED COMPOUNDS

[75] Inventors: Jean C. Miller; Gerald L. Thompson, both of Indianapolis, Ind.

[73] Assignee: Eli Lilly and Company, Indianapolis, Ind.

[21] Appl. No.: 220,471

[22] Filed: Dec. 29, 1980

[51] Int. Cl.$^3$ .................. C07D 519/04; A61K 31/475
[52] U.S. Cl. ................................ 260/244.4; 424/262
[58] Field of Search ...................... 260/244.4; 424/262

[56] References Cited

U.S. PATENT DOCUMENTS 4,029,663  4/1977  Gutowski et al. ................ 260/244.4
4,110,330  8/1978  Barnett et al. ................... 260/244.4

FOREIGN PATENT DOCUMENTS 1536407  12/1974  United Kingdom .

OTHER PUBLICATIONS

Barnett et al., J. Med. Chem., 21, 88, (1978).
Conrad et al., id, 22, 391, (1979).
Kutney et al., Can. J. Chem., 56, 42, (1974).
Kutney et al., Heterocycles, 6, 905, (1977).
Kutney et al., id, 3, 639, (1975).
Kutney et al., id, 3, 205, (1975).
Potier et al., J.C.S. Chem. Comm., 670, (1975).
Potier et al., J.A.C.S., 101, 2243, (1979).

*Primary Examiner*—Donald G. Daus
*Assistant Examiner*—Diana G. Rivers
*Attorney, Agent, or Firm*—James L. Rowe; Arthur R. Whale

[57] ABSTRACT

20'-Hydroxy derivatives of VLB, leurosidine and vincristine, antimitotic agents.

5 Claims, No Drawings

20'-HYDROXYVINBLASTINE AND RELATED COMPOUNDS

BACKGROUND OF THE INVENTION

The alkaloids obtainable from *Vinca rosea* (*Catharanthus rosea*) have been a most productive source of drugs which adversely affect the growth of experimental malignancies in mammals. Initially, only some of the alkaloids obtained from the leaves of the plant by extraction and purified by chromatography were found to be active antineoplastic agents. It was found that these antineoplastic Vinca alkaloids were dimeric indole-dihydroindole alkaloids representable by the formula:

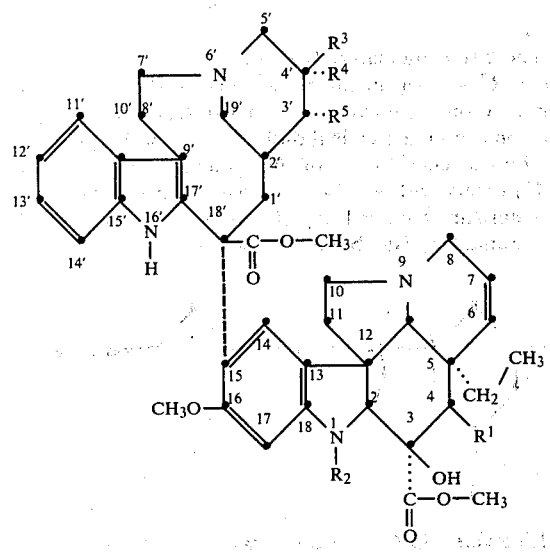

In the above formula where $R^1$ is acetoxy, $R^2$ is methyl, $R^3$ is hydroxyl, $R^4$ is ethyl and $R^5$ is H, vinblastine (vincaleucoblastine, VLB) is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl, and $R^5$ is H, leurosidine is represented; where $R^1$ is acetoxy, $R^2$ is methyl or formyl, $R^3$ is ethyl and $R^4$ and $R^5$ taken together form an α-epoxide ring, leurosine and leuroformine, respectively are represented. Literature references to the above alkaloids are as follows: leurosine (U.S. Pat. No. 3,370,057), VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220).

Two of the above alkaloids, vinblastine and vincristine, are now marketed for the treatment of malignancies, particularly the leukemias and related diseases, in humans. The two marketed alkaloids are customarily administered by the iv route. Two others, leurosidine and leuroformine, have been on clinical trial in the U.S. or in Europe.

Chemical modification of the Vinca alkaloids started slowly for several reasons. In the first place, the molecular structures involved are extremely complex, and chemical reactions which modify one specific functional group of the molecule without affecting other groups have been difficult to develop. Secondly, dimeric alkaloids lacking desirable chemotherapeutic properties have been recovered or produced from *Vinca rosea* extracts, and a determination of their structures has led to the conclusion that these inactive compounds are closely related structurally to, or are even isomeric with, the active alkaloids.

One of the more recent, and more successful, modifications of the basic indole-dihydroindole structure has been the preparation of C-3 carboxamide and carboxhydrazide derivatives. Many of these carboxamides are active anti-tumor agents (see U.S. Pat. No. 4,166,810, Barnett et al. *J. Med. Chem.*, 21 88 (1978) and Conrad et al., id, 22, 391 (1979). In particular, 4-desacetyl VLB C-3 carboxamide (vindesine) has proved to be very active in initial clinical tests and is currently on clinical trial in humans.

U.S. Pat. No. 4,029,663 discloses three anhydro derivatives each of 4-desacetylvinblastine and 4-desacetylvincristine. These derivatives were prepared by the action of cold concentrated sulfuric acid on vinblastine or vincristine respectively. Three different double bond isomers were formed in each case and were designated as, in the case of VLB, 3',4'-anhydro-4-desacetyl VLB; 4',20'-anhydro-4-desacetyl VLB (isomer 1); and 4',20'-anhydro-4-desacetyl VLB (isomer 2). The 4',20' isomers are double bond isomers in which the 21'-methyl is either above or below the plane of the vinblastine molecule.

Potier, Kutney and their associated research groups have prepared 3',4'-anhydrovinblastine by the use of a Polonovski fragmentation reaction involving the reaction of an $N_b$-oxide of catharanthine with vindoline in the presence of trifluoroacetic acid—see, for example, *J.C.S. Chem. Comm.* 670 (1975); British Patent Specification No. 1,536,407; *Tetrahedron Letters*, 1099, 3945 (1976); U.S. Pat. No. 4,144,237; *Heterocycles*, 3, 205, 639 (1975), 6, 905 (1977).

Functionalization of the double bond in 3',4'-anhydrovinblastine has proved difficult. Recently, Potier and his research group have reported the successful conversion of this compound (called by them $\Delta^{15'(20')}$-dehydrovinblastine) to vinblastine. This work is summarized in an article appearing in *J.A.C.S.*, 101, 2243 (1979).

Kutney et al., *Can. J. Chem.*, 56, 62 (1978) has also functionalized the 3',4'-double bond of 3',4'-anhydiovinblastine by oxidation with $OsO_4$ to produce leurosine.

20'-Hydroxy derivatives of 4-deacetyl vinblastine or other vinca alkoloids have not heretofore been reported, nor has derivatization of the 4',20'-anhydro-double bond in the 4',20'-anhydro 4-deacetyl VLB or vincristine isomers.

DESCRIPTION OF THE INVENTION

The compounds provided by this invention can be represented by the formula

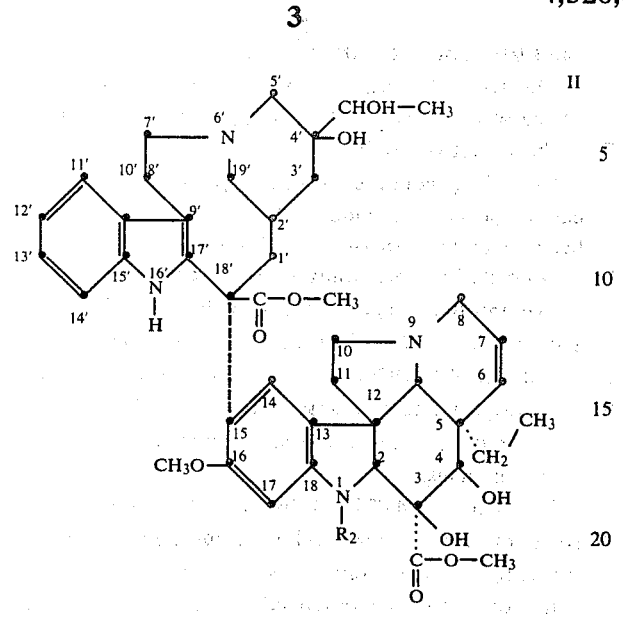

wherein $R^1$ is $CH_3$ or CHO.

The acid addition salts of the above compounds are also included within the scope of this invention.

Of particular interest are compounds according to II above represented by the formula

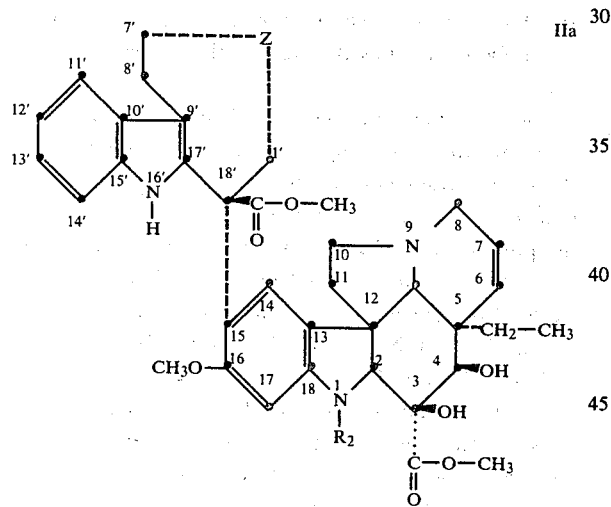

wherein Z is

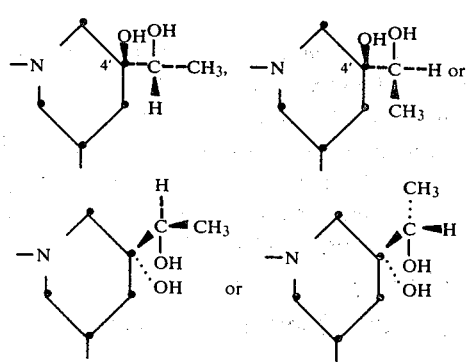

and $R^2$ is $CH_3$ or CHO.

The compounds of this invention are prepared by the reaction of $OsO_4$ on 4',20'-anhydro-4-desacetyl VLB exocyclic double bond isomers (and related double bond isomers) from U.S. Pat. No. 4,029,663. These starting materials are designated as Isomer 1 and Isomer 2 and can be represented by IIa above when Z is

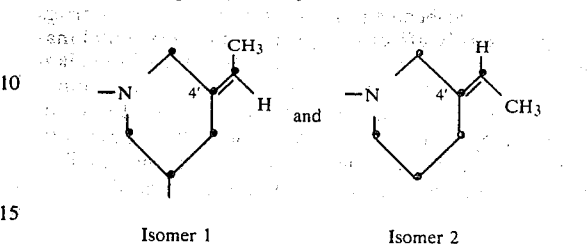

Isomer 1      Isomer 2

These starting materials are known for both instances when $R^2$ is $CH_3$(vinblastine series) or CHO (vincristine series). Osmium tetroxide ordinarily reacts with a double bond to give a vicinal diol in which both hydroxyls are on the same "side" of the molecule. For example, $OsO_4$ reacts with 4',20'-anhydro-4-desacetylvinblastine or vincristine Isomer 1 to yield the isomeric pair of diols represented by IIa above in which Z is

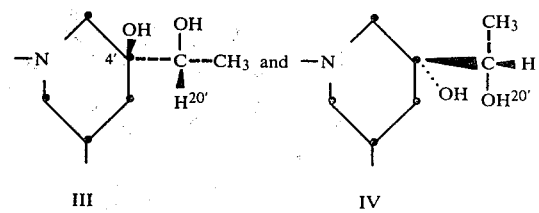

III      IV

Likewise $OsO_4$ reacts with 4',20'-anhydro-4-desacetylvinblastine or vincristine (Isomer 2) to yield two isomers in which Z is

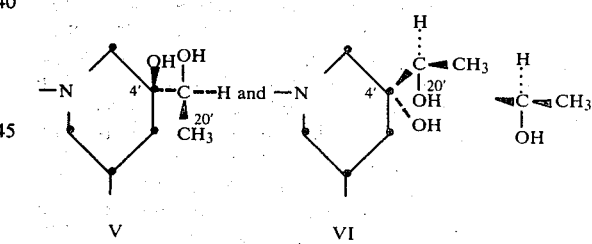

V      VI

In the above formulae, those isomers with a β-hydroxyl at C-4' belong to the vinblastine series (III and V) whereas those in which the 4'-hydroxyl has an α-orientation belong to the leurosidine series. Isomer III is named 20'-R-hydroxyvinblastine; IV is named 20'-S-hydroxyleurosidine; V is named 20'-S-hydroxyvinblastine; and VI is named 20'-R-hydroxyleurosidine.

Useful non-toxic acids for forming acid addition salts with the bases of this invention include inorganic acids such as: hydrochloric acid, nitric acid, phosphoric acid, sulfuric acid, hydrobromic acid, hydriodic acid, phosphorous acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, phosphite, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

More specifically, the compounds of this invention are prepared as follows. A 4',20'-anhydro VLB or vincristine isomer from U.S. Pat. No. 4,029,663 is reacted with osmium tetroxide in a mutual inert solvent such as THF in the presence of a small amount of water. The oxidation reaction is carried out at about 0° C. with stirring. The course of the reaction is followed by TLC. After TLC has shown that substantially all the starting material has been consumed, additional THF is added and gaseous hydrogen sulfide bubbled through the solution held at about 0° C. to reduce any residual osmium tetroxide. The products are isolated according to standard procedures and the two diasteroisomers produced by the oxidation are separated by chromatography.

This invention is further illustrated by the following specific example.

EXAMPLE 1

A reaction mixture was prepared containing 147.8 mg. of 4',20'-anhydro-4-desacetyl VLB (Isomer 2), 3 ml. of THF, and 8 drops of water. 50.4 Mg. of osmium tetroxide were added thereto and the resulting reaction mixture stirred at about 0° C. for one hour and then stored at that same temperature overnight. TLC revealed an absence of starting material. Six additional ml. of THF were added and $H_2S$ bubbled through the reaction mixture at about 0° C. for about 20 minutes after which time the resulting mixture was stirred at ambient temperature for 30 minutes. 4 Ml. of 50% aqueous ammonium hydroxide (prepared by adding 2 ml. of water to 2 ml. of 14 N aqueous ammonium hydroxide) were added and this reaction mixture stirred at ambient temperature for about 1.5 hours. An additional 10 ml. of 50% aqueous ammonium hydroxide were added plus 15 ml. of ethyl acetate. The resulting mixture was shaken in a separatory funnel and the contents filtered over celite. The celite was washed repeatedly with dilute aqueous ammonium hydroxide and with ethyl acetate. The combined washes were returned to the separatory funnel and the ethyl acetate layer separated. The aqueous layer was extracted four times with an equal volume of ethyl acetate. The ethyl acetate extracts were combined, washed with dilute ammonium hydroxide and then with saturated aqueous sodium chloride. Evaporation of the ethyl acetate in vacuo yielded a residue which was dried by adding toluene and removing the toluene azeotrope; yield = 85.2 mg. of a mixture of the two isomeric diols represented by formulas V and VI above when $R^2$ is $CH_3$. The mixture was purified by chromatography over 8 g. of silica. The eluant was a 20:1:1 ether-toluene-diethylamine mixture to which increasing quantities of methanol were added. First the column was eluted with 50 ml. of the above mixture containing 6% methanol, then with 50 ml. of the above mixture containing 9% methanol followed by 50 ml. of the above mixture containing 13% methanol and 50 ml. of the above mixture plus 20% methanol. Fractions shown by TLC to contain either of the above isomers were collected separately and combined and the solvent removed therefrom by evaporation in vacuo. 19.4 Mg. of 4-desacetyl-20'-S-hydroxy VLB (IIa wherein Z is structure V and $R^2$ is $CH_3$) and 23.5 mg. of 4-desacetyl-20'-R-hydroxyleurosidine (IIa where Z is VI and $R^2$ is $CH_3$) were obtained. 4-Desacetyl-20'-S-hydroxy VLB from Isomer 2 had the following physical characteristics.

Mass spectrum: m/e 798 (transmethylation), 784, 750, 725, 667, 587, 559, 427, 339, 311, 240, 205, 169, 119; Field desorption 784.

nmr (CDCl$_3$) 0.91, 1.07, 2.71, 3.55, 3.73, 3.80, 4.05, 5.78, 6.07, 6.44, 6.59, 7.988.

4-Desacetyl-20'-R-hydroxyleurosidine from Isomer 2 had the following mass spectrum: m/e 798 (transmethylation), 784, 740, 726, 681, 667, 587, 560, 427, 371, 240, 170, 135, 122, 107; Field desorption, 784.

The same reaction was carried out on 4',20'-anhydro-4-desacetyl VLB (Isomer 1) to yield a mixture of the diastereoisomers where Z is III or IV and $R^2$ is $CH_3$. The isomer mixture was isolated and the isomers separated by the same procedure yielding compounds having the following characteristics.

4-Desacetyl-20'-R-hydroxy VLB (from 4',20'-anhydro-4-desacetyl VLB Isomer 1) had the following mass spectrum: m/e 798 (transmethylation), 784, 753, 725, 667, 587, 427, 369, 355, 328, 295, 170, 154, 141; Field desorption 784.

Infrared spectrum (CHCl$_3$): 3670, 3550, 3490, 1720, 1650 (w), 1610, 1495, 1455, 1425 cm$^{-1}$.

4-Desacetyl-20'-S-hydroxyleurosidine (from 4',20'-anhydro VLB Isomer 1) had the following mass spectrum: m/e 812, 798 (both transmethylation), 784, 754, 740, 726, 681, 667, 623, 587, 570, 427, 393, 371, 329, 240, 170, 149, 135, 111, 107; Field desorption 784.

The corresponding vincristine diols are prepared similarly.

The compounds of this invention are mitotic inhibitors, inducing metaphase arrest in Chinese hamster ovary cells maintained in tissue culture using a procedure adapted from that of Siminoff, *Applied Microbiology*, 9, 66–72 (1961). Following such a procedure, 4-desacetyl-20'-R-hydroxy VLB (from 4',20'-anhydro-4-desacetyl VLB Isomer (1) showed a + + inhibition at 2 mcg/ml, 4-desacetyl-20'-S-hydroxy VLB (from 4',20'-anhydro-4-desacetyl VLB Isomer (2) showed a + inhibition at 2 mcg/ml as did 4-desacetyl-20'-S-hydroxyleurosidine (also from 4',20'-anhydro-4-desacetyl VLB Isomer 1). VLB shows a + + inhibition at 0.02 mcg/ml.

The compounds of this invention, being mitotic inhibitors, are potentially useful in the treatment of tumors in animals. As such, they would be administered by the iv route as are VLB and vincristine and should be used against the same tumors, at least initially, against which VLB and vincristine are active.

In addition, the compounds are intermediates; eg, they can be activated to form a 4,20'-diacyl derivative or can be oxidized.

We claim:

1. A compound of the formula:

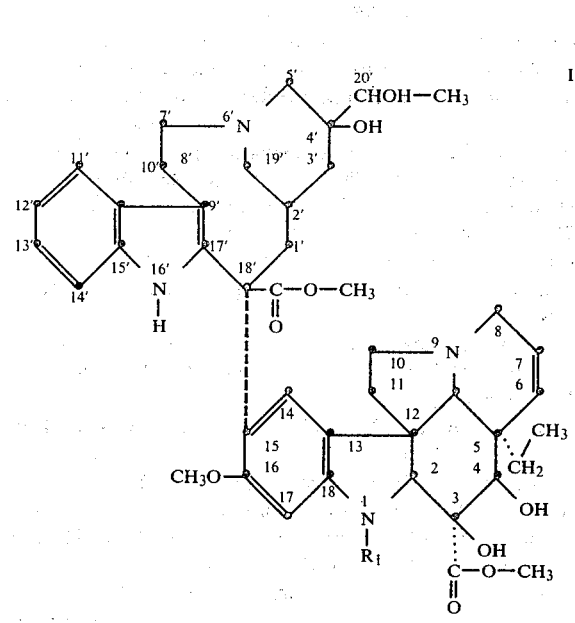

wherein R[1] is CH[3] or CHO, and acid addition salts thereof.

2. A compound of the formula

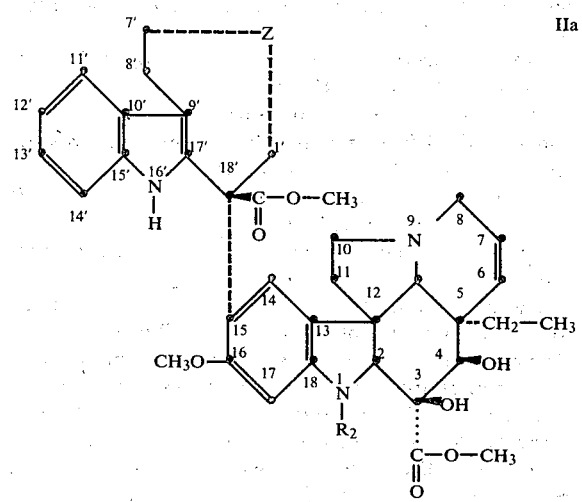

wherein Z is

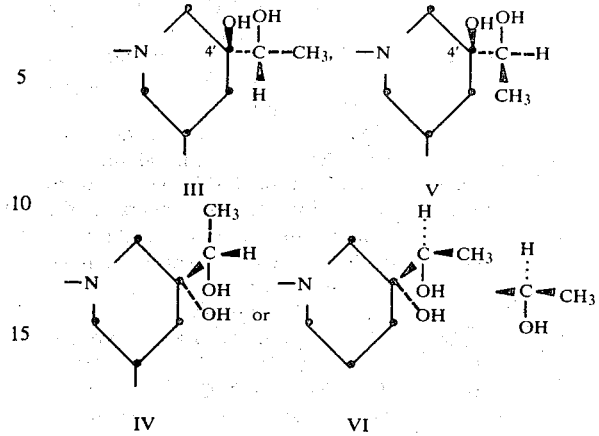

and R[2] is CH[3] or CHO.

3. A compound according to claim 2, in which Z is

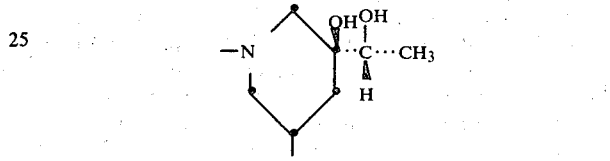

said compound being 4-desacetyl-20′-R-hydroxy VLB.

4. A compound according to claim 2 in which Z is

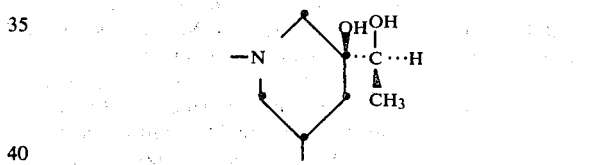

said compound being 4-desacetyl-20′-S-hydroxy VLB.

5. A compound according to claim 2 in which Z is

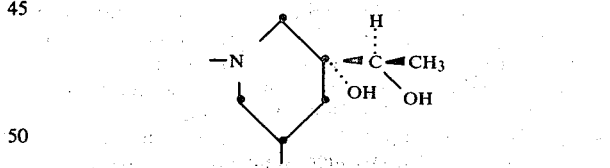

said compound being 4-desacetyl-20′-R-hydroxyleurosidine.

* * * * *